US012716860B2

(12) United States Patent
Goodrich et al.

(10) Patent No.: US 12,716,860 B2
(45) Date of Patent: Aug. 25, 2026

(54) PRINTED POTENTIOMETRIC SENSORS TO MEASURE ION CONCENTRATION IN SOIL

(71) Applicant: The Regents of the University of California, Oakland, CA (US)

(72) Inventors: Payton Goodrich, Berkeley, CA (US); Ana Claudia Arias, Lafayette, CA (US); Carol Baumbauer, Berkeley, CA (US); Margaret E. Payne, Sunnyvale, CA (US); Anju Toor, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 235 days.

(21) Appl. No.: 18/692,747

(22) PCT Filed: Sep. 16, 2022

(86) PCT No.: PCT/US2022/076527
§ 371 (c)(1),
(2) Date: Mar. 15, 2024

(87) PCT Pub. No.: WO2023/044405
PCT Pub. Date: Mar. 23, 2023

(65) Prior Publication Data

US 2024/0377349 A1 Nov. 14, 2024

Related U.S. Application Data

(60) Provisional application No. 63/261,330, filed on Sep. 17, 2021.

(51) Int. Cl.
*G01N 27/403* (2006.01)
*G01N 27/30* (2006.01)
(Continued)

(52) U.S. Cl.
CPC ....... *G01N 27/4035* (2013.01); *G01N 27/301* (2013.01); *G01N 27/3335* (2013.01); *G01N 33/245* (2024.05)

(58) Field of Classification Search
CPC ............. G01N 27/4035; G01N 27/301; G01N 27/3335; G01N 33/245
See application file for complete search history.

(56) References Cited

U.S. PATENT DOCUMENTS

2012/0279298 A1 11/2012 Etheridge et al.
2015/0177183 A1* 6/2015 Bakker ............. G01N 27/3335 204/295

(Continued)

FOREIGN PATENT DOCUMENTS

WO 2020025688 A1 2/2020
WO 2020193974 A1 10/2020

OTHER PUBLICATIONS

Rosenberg et al., "In-field determination of soil ion content using a handheld device and screen-printed solid-state ion-selective electrodes," PLOS One Sep. 25, 2018 (Year: 2018).*

(Continued)

*Primary Examiner* — Alexander S Noguerola

(57) ABSTRACT

An example apparatus is disclosed. The apparatus includes a reference electrode and an ion selective electrode (ISE). The reference electrode includes a reference electrode substrate, a reference electrode conductor formed via a printable composition on the reference electrode substrate, and a reference membrane formed on the carbon nanotube layer. The ISE includes an ISE substrate, a ISE conductor printed on the substrate via a printable composition on the ISE substrate, and an ion-selective membrane printed on the conductor via a printable membrane solution.

20 Claims, 12 Drawing Sheets

(51) Int. Cl.
*G01N 27/333* (2006.01)
*G01N 33/24* (2006.01)

(56) References Cited

U.S. PATENT DOCUMENTS

| | | | | |
|---|---|---|---|---|
| 2017/0045487 | A1* | 2/2017 | Bauer-Reich | H04B 7/1851 |
| 2018/0136160 | A1* | 5/2018 | Chumbimuni-Torres | G01N 27/3335 |
| 2019/0339225 | A1 | 11/2019 | Jank et al. | |
| 2020/0096474 | A1* | 3/2020 | Mansergh | G01N 33/246 |
| 2020/0116664 | A1 | 4/2020 | Darshani et al. | |
| 2021/0302351 | A1* | 9/2021 | Andrade | G01N 33/48707 |
| 2022/0291164 | A1* | 9/2022 | Zhang | G01N 27/3335 |
| 2023/0296548 | A1* | 9/2023 | Syrovy | G01K 7/16 324/664 |
| 2024/0077446 | A1* | 3/2024 | Sui | G01N 33/245 |

OTHER PUBLICATIONS

Rius-Ruiz et al., "Disposable Planar Reference Electrode Based on Carbon Nanotubes and Polyacrylate Membrane," Anal. Chem. 2011, 83, 5783-5788 with Supporting Information (Year: 2011).*

DuPont™ 7102 Carbon Conductor, MatWeb Material Priperty data, 2025, https://www.matweb.com/search/datasheet.aspx?matguid=adbb23fd31104998b11efa871087e4a1&ckck=1 (Year: 2025).*

P. Sjoberg et al., "Paper-based potentiometric ion sensors constructed on ink-jet printed gold electrodes," Elsevier, Sensors and Actuators B: Chemical, vol. 224; dated Oct. 19, 2015, 8 pages. http://dx.doi.org/10.1016/j.snb.2015.10.051.

Extended European Search Report, Application No. 22870967.1-1001, dated Apr. 17, 2025, 12 pages.

Zamarayeva et al., Optimization of printed sensors to monitor sodium, ammonium, and lactate in sweat, APL Materials, vol. 8, No. 100905, Oct. 15, 2020.

Baumbauer et al., "Printed Potentiometric Nitrate Sensors for Use in Soil, Sensors," vol. 22, May 28, 2022, pp. 1-13.

International Search Report and Written Opinion, PCT/US2022/076527, Jan. 20, 2023, 12 pages.

* cited by examiner

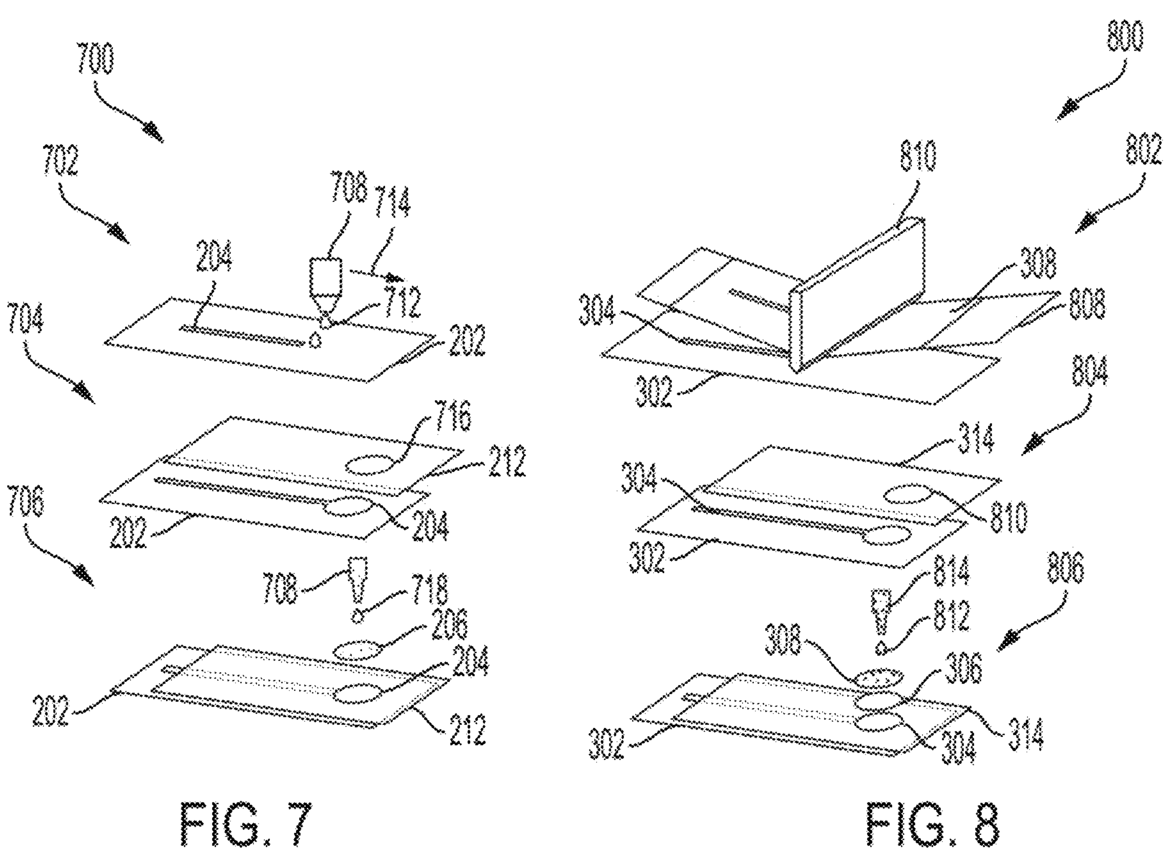
FIG. 7
FIG. 8
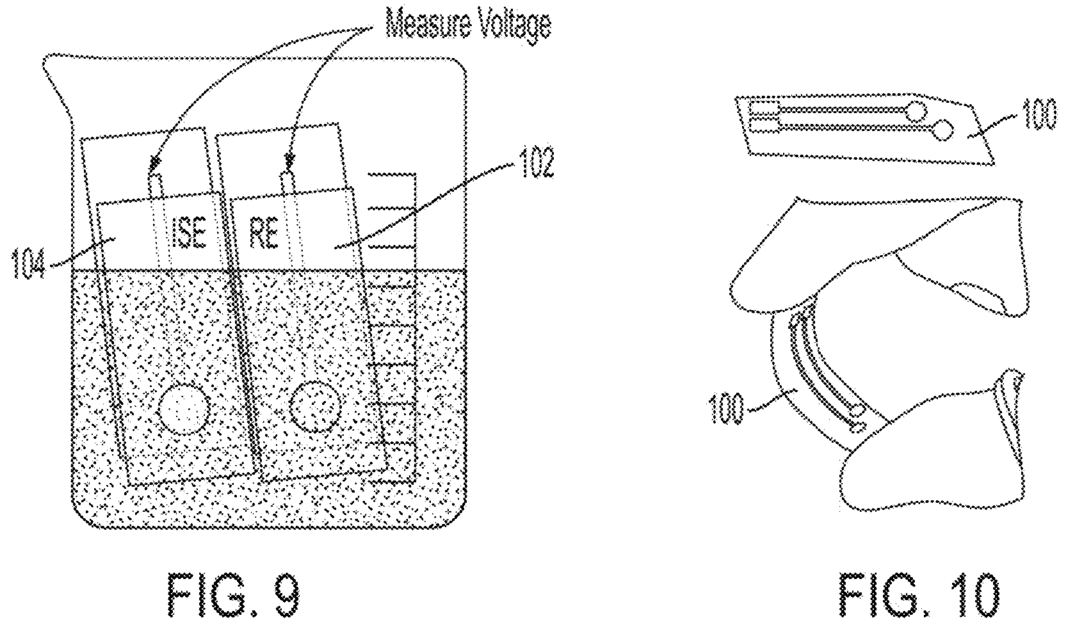
FIG. 9
FIG. 10

1200

| Run | $NO_3^-$ (ppm) | $P_2O_5$ (ppm) | $K^+$ (ppm) | $Mg^{2+}$ (ppm) | $SO_4^{2-}$ (ppm) |
|---|---|---|---|---|---|
| 1 | 25 | 60 | 475 | 180 | 11 |
| 2 | 10 | 60 | 150 | 60 | 20 |
| 3 | 10 | 20 | 800 | 300 | 11 |
| 4 | 25 | 100 | 800 | 300 | 20 |
| 5 | 10 | 20 | 150 | 300 | 2 |
| 6 | 10 | 100 | 150 | 300 | 20 |
| 7 | 10 | 100 | 475 | 60 | 2 |
| 8 | 40 | 20 | 800 | 60 | 2 |
| 9 | 40 | 100 | 150 | 60 | 11 |
| 10 | 25 | 20 | 150 | 60 | 2 |
| 11 | 10 | 100 | 800 | 180 | 2 |
| 12 | 40 | 20 | 150 | 180 | 20 |
| 13 | 40 | 20 | 475 | 300 | 20 |
| 14 | 40 | 60 | 800 | 300 | 2 |
| 15 | 10 | 20 | 800 | 60 | 20 |
| 16 | 40 | 100 | 150 | 300 | 2 |
| 17 | 40 | 100 | 800 | 60 | 20 |

FIG. 12A

PRINTED POTENTIOMETRIC SENSORS TO MEASURE ION CONCENTRATION IN SOIL

CROSS-REFERENCE TO RELATED APPLICATIONS

This application is a 371 U.S. National Phase Application of International Application No. PCT/US22/76527, filed on Sep. 16, 2022, which claims the benefit of U.S. Provisional Patent Application No. 63/261,330 filed on Sep. 17, 2021; both of which are hereby incorporated by reference in their entirety.

REFERENCE TO GOVERNMENT FUNDING

The invention was made with government support under Grant Number DE-AR0001013 awarded by the United States Department of Energy. The government has certain rights in the invention.

FIELD OF THE INVENTION

The present disclosure relates generally to printed potentiometric sensors to measure ion concentrations in soil.

BRIEF DESCRIPTION OF THE DRAWINGS

The teaching of the present disclosure can be readily understood by considering the following detailed description in conjunction with the accompanying drawings, in which:

FIG. 7 illustrates an example fabrication process of the ISE of the present disclosure;

FIG. 8 illustrates an example fabrication process of a reference electrode of the present disclosure;

FIG. 9 illustrates an example of the reference electrode and the ISE on a same substrate;

FIG. 10 illustrates an example of the printed reference electrode and the ISE;

FIGS. 12A and 12B illustrate example data of ion concentrations of various runs with the printed potentiometric sensor of the present disclosure;

To facilitate understanding, identical reference numerals have been used, where possible, to designate identical elements that are common to the figures.

DETAILED DESCRIPTION

The present disclosure provides examples of printed potentiometric sensors to measure ion concentrations in soil. In some examples, the potentiometric sensors can be printed from biodegradable materials that can be left in the soil and allow to biodegrade over time. The potentiometric sensors can be deployed as a sensor array that can measure concentrations of different ions.

Nitrogen, especially nitrate (NO3-N) is one of the main components of the fertilizers used in agriculture. Because nitrate is highly mobile, nitrogen applied in agricultural settings can easily leach into groundwater, where it contaminates well water used for drinking. Excess nitrate (above 10 ppm) in drinking water is known to cause adverse outcomes to human health. Nitrates can also run off into surface water and accumulate in still bodies of water which can lead to harmful algal blooms and eutrophication. Therefore, applying too much nitrate is not just wasteful and expensive, it also has harmful impacts on the environment and human health.

State of the art nitrate measurements in both soil and water quality monitoring involve taking samples from the environment or field to a laboratory, where they can be analyzed with chromatography or spectrographic methods. Such measurements are highly accurate, but they are also expensive and labor-intensive, and give data for only one point in time and space. To better characterize the nitrate problem, and better tailor nitrogen fertilizer inputs in agriculture, the present disclosure provides a printed potentiometric sensor.

Figure 1:
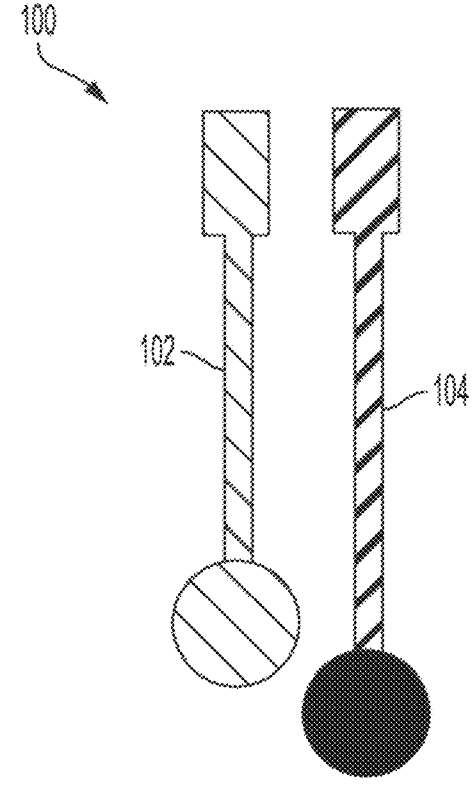
FIG. 1 illustrates a block diagram of an example printed potentiometric sensor of the present disclosure.

Printed potentiometric sensors represent a viable approach for distributed environmental nitrate sensing as the materials and deposition techniques used in their fabrication allow high through put fabrication and the electronics required for data read-out are readily available. FIG. 1 illustrates an example printed potentiometric sensor 100 that includes a reference electrode 102 and an ion-selective electrode (ISE) 104. Although a single ISE 104 is illustrated in FIG. 1, it should be noted that the sensor 100 may include an array of different ISEs 104 that can be used to measure concentrations of different ions in the soil that are to be detected.

Figure 2:
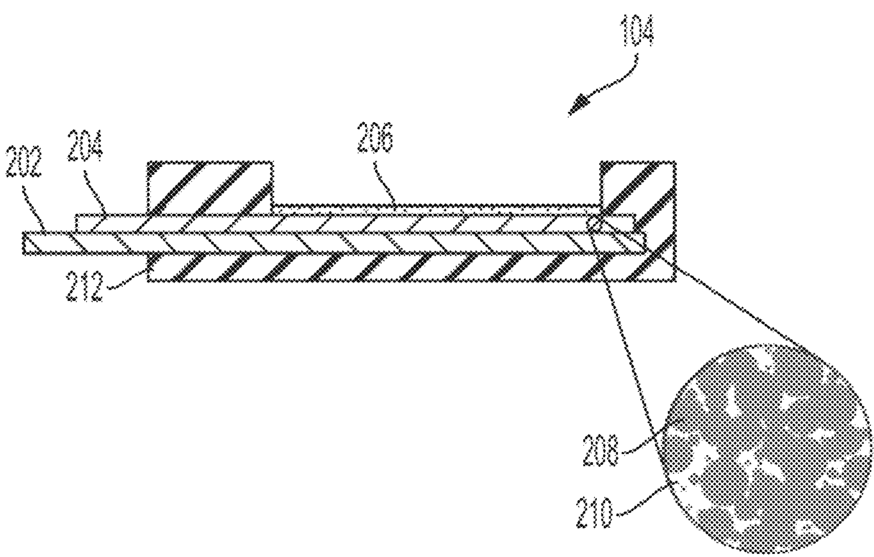
FIG. 2 illustrates a block diagram of an example ion-selective electrode (ISE) of the present disclosure.

FIG. 2 illustrates a cross-sectional view of each layer of an example of the ISE 104. In one embodiment, the ISE 104 may include a substrate 202, a conductor 204, and an ion-selective membrane (ISM) 206. The ISE 104 may be encapsulated by an encapsulant 212 to shield the ISE 104 from impact and corrosion in the soil.

Figure 16:
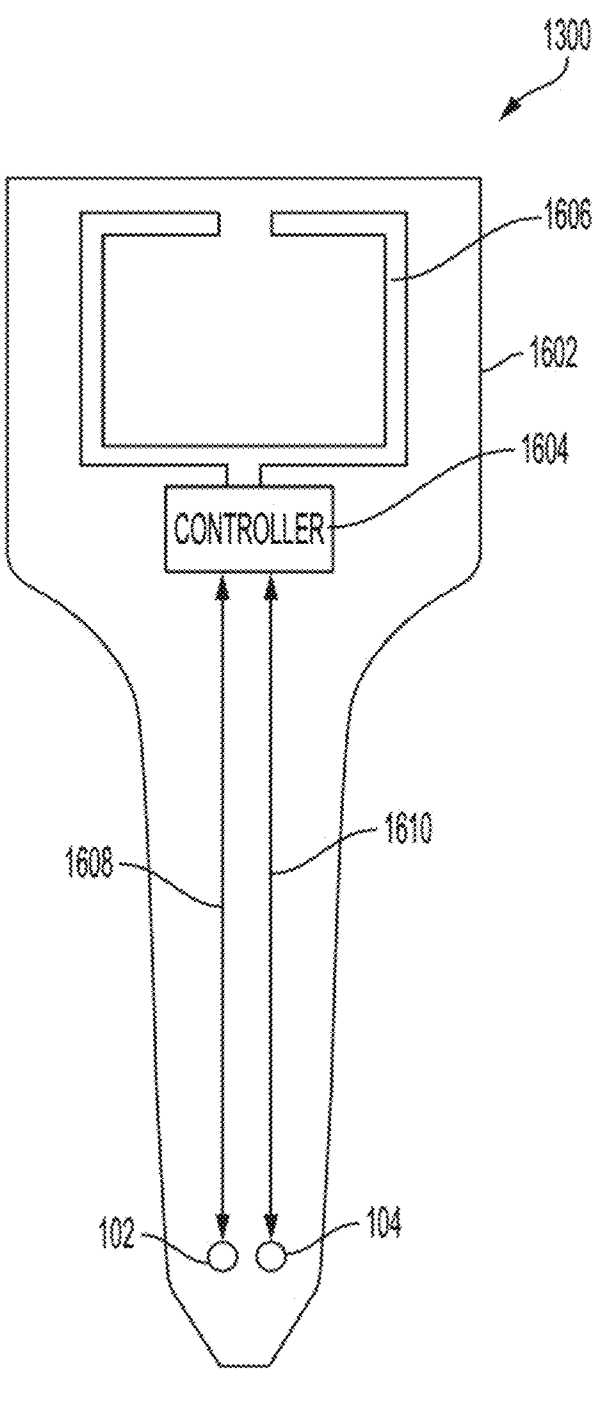
FIG. 16 illustrates an example block diagram of a sensor assembly of the present disclosure.

In one embodiment, the substrate 202 may provide surface properties that allow conductive ink to print onto the substrate 202. The conductor 204 carries data as an electrical potential from the electrode to the communications integrated circuit (IC). An example of a sensor assembly IC is illustrated in FIG. 16, and discussed in further details below.

The conductor 204 may include a binder 210 and conductive particles 208. The conductive particles 208 may form a percolated network to conduct electricity after drying. The binder 210 may "glue" the conductive particles 208 in place.

In one embodiment, the ISM 206 may include a structural polymer, a plasticizer, an ionophore, and a charge carrier. The structural polymer may be any type of plastic that is compatible with the materials of the ISE 104. In one embodiment, the structural polymer may be polyvinyl chloride (PVC). The plasticizer may be used to solvate the structural polymer to make the structural polymer solution processable. The resulting membrane is a solvent dispersed uniformly in the PVC matrix. As a result, the ISM 206 may be printed using a printhead to dispense the ISM 206 on to desired locations of the substrate 202.

In one embodiment, the ionophore may provide bonding sites that are selective to an ion of choice. The type of ionophore that is selected may be based on the ion that is to be measured in the soil. The bonding sites may be provided in a ring shape molecule. In one embodiment, the charge carrier decreases the number of uncomplexed (e.g., unbonded) ions in the membrane.

Figure 3:
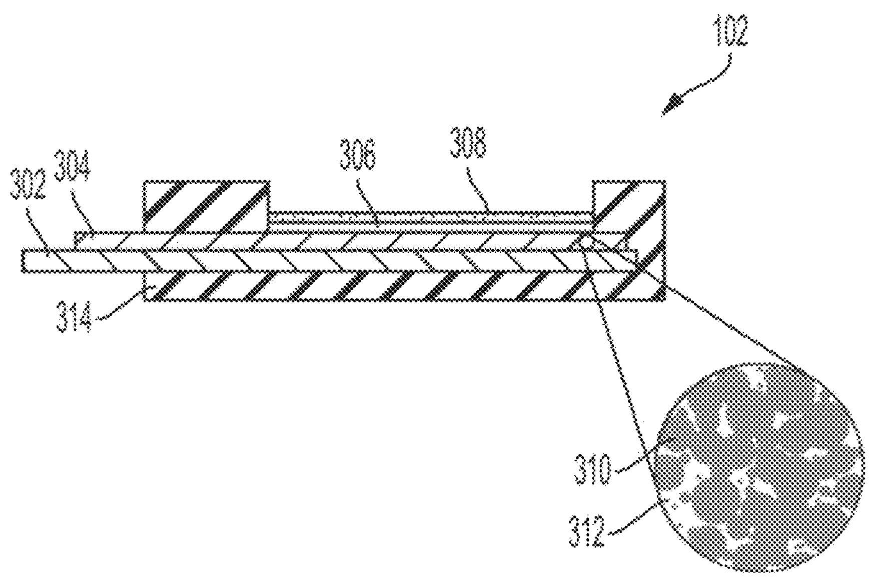
FIG. 3 illustrates a block diagram of an example reference electrode of the present disclosure.

FIG. 3 illustrates a cross-sectional view of each layer of an example of the reference electrode 102. The reference electrode 102 may include a substrate 302, a conductor 304, a carbon nanotube (CNT) layer 306, and a reference membrane 308. The reference electrode 102 may be encapsulated by an encapsulant 314 to shield the reference electrode 102 from impact and corrosion in the soil.

In one embodiment, the conductor 304 may carry data as an electrical potential from the electrode to the communications IC. The conductor 304 may include a binder 312 and conductive particles 310. The conductive particles 310 may form a percolated network to conduct electricity after drying. The binder 312 may "glue" the conductive particles 310 in place.

In one embodiment, the CNT layer 306 may include carbon nanotubes. The CNT layer 306 may increase the surface area for the silver/silver chloride (Ag/AgCl) reaction to take place. The CNT layer 306 may be optional.

In one embodiment, the reference membrane 308 may include a structural polymer, a salt, and a chloride compound. The polymer may be any type of plastic that is compatible with the materials of the reference electrode 102. In one embodiment, the polymer may be polyvinyl butyral (PVB). The PVB provides the structure.

The salt may be optional and may be any type of salt specific to the ion being measured. For example, for a nitrate sensor, the salt may be a nitrate salt. For an ammonium sensor, the salt may be an ammonium salt. For a potassium sensor, the salt may be a potassium salt, and so forth.

The chloride compound may be any type of ionic chloride compound or salt. For example, the chloride compound may include sodium chloride, potassium chloride, calcium chloride, and the like.

In the example of a nitrate sensor where a nitrate salt and sodium chloride is used, the nitrate salt decreases the sensitivity of the reference electrode in a nitrate solution. The sodium chloride is saturated in the membrane to ensure the Ag/AgCl reaction is not rate-limiting.

Figure 4:
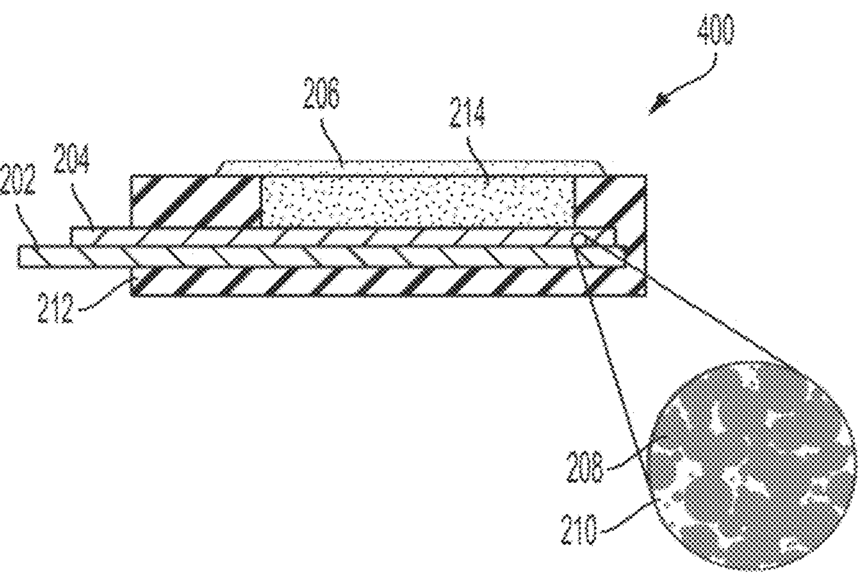
FIG. 4 illustrates a block diagram of another example ISE electrode of the present disclosure.

FIG. 4 illustrates a cross-sectional view of another embodiment of an ISE 400 of the present disclosure. The ISE 400 may be of similar composition to the ISE 104 except that the ISE 400 includes an ion-to-electron transduction layer 214. For example, the ISE 400 may include the substrate 202, the conductor 204, and the ISM 206. The conductor 204 may include the binder 210 and the conductive particles 208.

In one embodiment, the ion-to-electron transduction layer 214 may be a filling solution or mediator solution for the transport of ions to the electrode surface. The filling solution may be responsible for arbitrating the build-up of electrical charge or potential from a concentration of ions that are being measured in the soil.

In other embodiments, the ion-to-electron transduction layer 214 may not necessarily be a solution. For example, the ion-to-electron transduction layer may be a solid electrolyte or a high surface area capacitive transducer.

Figure 5:
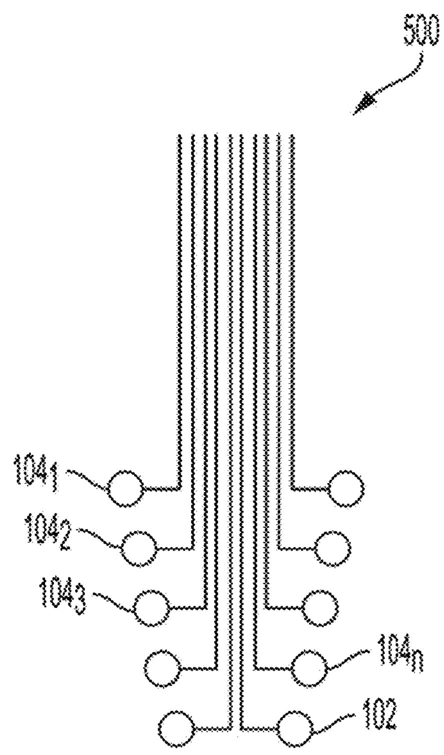
FIG. 5 illustrates a block diagram of an example printed potentiometric sensor array of the present disclosure.

FIG. 5 illustrates a printed potentiometric sensor array 500 that includes a plurality of different ISEs 1021 to 102*n* (hereinafter referred to individually as an ISE 102 or collectively as ISEs 102) to detect different ions in the soil. For example, the array 500 may include an ISE 1021 that is a nitrate selective electrode, an ISE 1022 that is an ammonium selective electrode, an ISE 1023 that is a phosphate selective electrode, or any other analyte selective electrode to measure a particular analyte that could be found in soil. The array 500 may also include the reference electrode 102.

The reference electrode 102 may be of similar composition and geometry to the reference electrode 102 illustrated in FIG. 3 and described above. The various electrodes to measure different ions illustrated in FIG. 5 may be similar to the ISE 104 illustrated in FIG. 2, except for the ISM 206, which may be different for each different electrode. For example, a nitrate ionophore may be used in the membrane of the nitrate selective electrode, an ammonium ionophore may be used in the membrane of the ammonium selective electrode, and so forth.

FIG. 16 illustrates an example of a sensor assembly 1600. The sensor assembly 1600 may include a communications IC to allow the reference electrode 102 and the ISE 104 to communicate electrical data that is correlated to concentrations of a particular ion being measured in the soil.

In one embodiment, the sensor assembly 1600 may include a stake 1602. The stake 1602 may be fabricated from a biodegradable material. For example, the stake 1602 may be fabricated from wood or a wax soaked wooden stake.

The reference electrode 102 and the ISE 104 may be printed onto the stake 1602. The sensor assembly 1600 may also include a controller 1604 and an antenna 1606. In one embodiment, the antenna 1606 may be a loop antenna that can be printed onto the stake 1602.

The controller 1604 may be a processor and/or a radio frequency identification (RFID) chip, WiFi chip, Bluetooth chip, near field communications (NFC) chip, a cellular communications chip, or any other chip to provide transmission of the data. The controller 1604 may be communicatively coupled to the reference electrode 102 and the ISE 104 via conductive traces 1608 and 1610. The controller 1604 may collect the electrical data collected by the reference electrode 102 and the ISE 104 via the conductive traces 1608 and 1610 and transmit them to a collection server (not shown) via the antenna 1606. The collection server may then convert the electrical data to actual concentration values of the measured ions in the soil.

As discussed above, reference electrodes are typically fabricated with Ag/AgCl and maintain a constant potential in varying ionic environments. Ion selective electrodes are made of a conductive material and an ISM. These membranes include an ionophore which selectively and reversibly binds with the ion of interest, held in a structural polymer matrix. When the ion of interest binds to the hydrophilic sites in the ionophore membrane, a change in the potential at the surface of the ion selective electrode is observed, which is measured with respect to the reference electrode. This potential difference is used to determine the concentration of ion present based on the Nernst Equation.

The present disclosure provides printed potentiometric sensors 100 that may also be fabricated from biodegradable materials. Printing enables the fabrication of the sensors 100 at a large scale. Printing encompasses a variety of solution processing techniques, which allow material to be deposited over large areas at high speeds and low temperatures. Printing is also compatible with a wide variety of solution processable materials, including conductors and polymeric materials. Unconventional active materials can be solution processed and deposited with a variety of printing techniques.

Printed nitrate sensors should show high sensitivity to nitrate throughout a broad range of nitrate concentrations and should be insensitive to other ions. Soil is a complex environment containing many ions which could interfere with a nitrate sensor. To efficiently quantify the interference of six interfering species in the laboratory a set of definitive screening designs can be used.

In the present disclosure, an example of the sensor 100 was fabricated with an ISM 206 to measure nitrates in soil. The sensitivity of the sensor 100 to NO3-N was measured. The sensitivity of the ISEs 104 was measured against commercially available reference electrodes and demonstrated a near-Nernstian response to nitrate. Selectivity of the nitrate ISE 104 was evaluated against several ions found in soil using the Definitive Screening Design, which showed that the electrodes were insensitive to phosphate (P2O5), potassium, magnesium, and sulfate, but minimally sensitive to chloride and nitrite at levels relevant for soil. A formulation of a printed reference electrode 102 was developed and the stability of the reference electrode 102 in nitrate solutions was tested. Finally, the printed nitrate ISE 104 was paired with a printed reference electrode 102 to create a fully printed nitrate sensor 100. Although the below examples describe a potentiometric nitrate sensor, it should be noted that any type of ionophore may be selected for the ISM to detect the desired concentration of a particular ion.

In an example, the ISM 206 were fabricated with Nitrate Ionophore VI, dibutyl phthalate, tetraoctylammonium chloride, poly(vinyl chloride) (PVC), and tetrahydrofuran (THF), obtained from Millipore Sigma. Butvar B-98 (poly (vinyl butyral) or PVB), poly(ethylene glycol)-block-poly (propylene glycol)-block-poly (ethylene glycol) diacrylate (F127), and methanol were obtained from Millipore Sigma for the preparation of reference electrode membranes. Single Walled Carbon Nanotubes (CNTs) were obtained from Carbon Solutions, Inc for making reference electrode membranes.

For the sensitivity and selectivity studies, powdered NaNO3, KNO3, NaNO2, KCl, Na2SO4, MgCl2, Ca(NO3)2, and NaCl were obtained from Millipore Sigma. Pelletized KNO3 (13-0-45) and NH4NO3 (33-0-0) fertilizers were obtained from Nutrien Ag Solutions (Belgrade, MT, USA). Monopotassium Phosphate Fertilizer (0-52-34) was obtained from Greenway Biotech, Inc. as the source of P2O5 and K2O.

Commercial Ag/AgCl reference electrodes were obtained from Koslow Scientific (1004) and Millipore Sigma (Z113107). Chronopotentiometery was performed using the Keithley 2400 Series SourceMeter, Keysight B2987A Electrometer/High Resistance Meter, and Ivium-n-Stat from Ivium Technologies B.V.

Gold electrodes were printed using Harima Nanopaste (Au) NPG-J gold ink in a Dimatix inkjet printer at ambient conditions. Printed gold electrodes were sintered at 250° C. for 50 minutes. Ag/AgCl was screen printed using Engineered Materials Systems, Inc. CI-4001 ink. Three layers of ink were printed; each layer was dried before the next was printed. Printed Ag/AgCl electrodes were then annealed at 120. C in a vacuum oven for 2 hours. All electrodes were printed on PQA2 PEN 25 μm thick. Printed electrodes were encapsulated with laser-cut Teflon tape 75 μm thick and have circular active areas of 3 mm diameter, resulting in an active area of 0.07068 cm2.

ISEs were fabricated by mixing Nitrate Ionophore VI 5.2 wt %, dibutyl phthalate 47.1 wt %, tetaroctylammonium chloride 0.6 wt %, and PVC 47.1 wt % in solution. A total of 0.2 g of this mixture was dissolved in 1.3 mL of THF. Six μL of this solution was drop-cast in three 2 μL increments on the printed ISE surface. The resulting ISE dried in a fume hood for 15 minutes.

The reference electrodes employed a CNT transducer between the Ag/AgCl electrode and the membrane. This transducer was composed of 0.01 g of CNT and 0.05 g of F127 dissolved in 10 mL of THF, which were sonified for 1 hour in an ice bath using a Branson Digital Sonifier probe. The resulting mixture was deposited on the printed reference electrode surface as 4 μL 101 total in two separate 2 μL increments.

The reference electrode employing the PVB and NaCl membrane was made by dissolving 1.58 g of PVB and 1.00 g of NaCl in 20 mL of methanol. This mixture was sonified for 30 minutes in an ice bath. The resulting mixture was deposited on top of the CNT transducer as 6 μL total in three separate 2 μL increments.

To perform sensitivity measurements, $NaNO_3$ was dissolved in deionized water, and diluted to 0.01, 0.05, 0.1, 0.5, 1, 5, 10, 20, 50, and 100 mM concentrations. Sensitivity studies with varying nitrate salts used 100, 10, 1, and 0.1 mM solutions of $NaNO_3$, $KNO_3$, and $NH_4NO_3$.

Reference electrode sensitivity measurements were made in both $NaNO_3$ and $NH_4NO_3$ diluted in DI water in concentrations between 0.01 mM and 100 mM.

Solutions for screening experiments were made by dissolving solutes in deionized water. The generation of the experiment design tables and data analysis were performed using the design of experiments platform of the statistical software JMP 14 (SAS, Cary, USA).

For the selectivity screening experiments, $NaNO_3$ was used as the source of NO3, commercially available water-soluble Monopotassium Phosphate Fertilizer (0-52-34) containing $P_2O_5$ and $K_2O$ was used as the source of $P_2O_5$, the same water-soluble fertilizer augmented with KCl was used as the source of K+, $MgCl_2$ was used as the source of $Mg^{2+}$, and $Na_2SO_4$ was used as the source of $SO_4^{2-}$. A single solution was made for each of the 17 runs outlined in a Table 1200 illustrated in FIG. 12A, including concentration of each chemical for each run. The ion selective electrode potential was measured against a commercial Ag/AgCl reference electrode in each solution to obtain the results in the graphs 1202 illustrated in FIG. 12B.

An example fabrication process 700 of the ISE 104 is illustrated in FIG. 7. At step 702, a printhead 708 may be used to dispense conductive ink 712 that is used to print the conductor 204 or conductive trace. In an example, the conductive ink 712 may be gold ink that forms the conductive trace of the ISE 104.

At step 704, the conductor 204 is encapsulated by the encapsulant 212. In one embodiment, the encapsulant 212 may be a piece of teflon with a hole 716 pre-cut for the electrode's active area.

At block 706, a membrane solution 718 is deposited in an active area defined by a portion of the conductor 204 that is exposed via the hole 716 in the encapsulant 212. The membrane solution 718 is deposited to print the ISM 206. The membrane solution 718 is allowed to dry.

An example fabrication process 800 of the reference electrode 102 is illustrated in FIG. 8. At step 802 the conductor 304 or conductive trace is screen printed onto the substrate 302 using a screen 808. The conductive solution may be deposited over the screen 808 and onto the substrate 302. A squeegee or blade 810 may be used to evenly coat the conductive solution onto the substrate 302. In one embodiment, the conductor 304 may be Ag/AgCl.

At step 804, the conductor 304 is encapsulated by the encapsulant 314. In one embodiment, the encapsulant 314 may be Teflon with a pre-cut hole 810.

At step 806, a printhead 814 may be used to dispense the CNT layer 306 and a membrane solution 812. Although a single printhead 814 is illustrated in step 806, it should be noted that different printheads 814 may be used to dispense the CNT layer 306 and the membrane solution 812. The CNT layer 306 may be drop cast from solution onto the active area defined by a portion of the conductor 304 that is exposed via the hole 810 in the encapsulant.

In one embodiment, the membrane solution 812 may be dispensed in the active area on the CNT layer 306. The membrane solution 812 is deposited to print the reference membrane 308. The membrane solution 812 may then be dried.

Although FIGS. 7 and 8 illustrate one example of fabricating the sensor 100, it should be noted that other methods of fabrication may be deployed. As noted above, the sensor assembly 1300 may be a biodegradable sensor assembly. In one embodiment, the sensory assembly 1300 may be fabricated by soaking a basswood stake in molten beeswax and cooled. The wax surface may be smoothed on each side with a heated doctor blade. The antenna 1606 and the conductive traces 1608 and 1610 may be screen printed with a zinc composite ink and then electrochemically sintered. The conductor layers 204 and 304 may be blade coated on top of the conductive traces 1608 and 1610. For example, a biodegradable conductor 204 may be a carbon ion-selective electrode and the conductor layer 304 may be Ag/AgCl. The controller 1604 (e.g., an RFID integrated circuit) may be bonded to the conductive traces 1608 and 1610 connected to electrically connect the reference electrode 102 and the ISE 104 to the controller 1604. The sensor assembly may be encapsulated with a wax-soaked paper scaffold. Lastly, the CNT layer 306, the reference membrane 308, and the ISM 206 may be drop cast onto the conductive layers 204 and 304.

When an ISE 104 and a reference electrode 102 are in electrochemical contact with each other, the potential voltage difference between the two electrodes when no current is flowing corresponds to the concentration of nitrate in the solution, as shown in FIG. 9. FIG. 9 shows the printed reference electrode 102 and the printed ISE 104 on the same substrate and placed in a solution to measure concentration based on a measured voltage. The potential in a potentiometric sensor is described by the Nernst equation:

$$E = E0 + 2.3026(RT)/(zF)\log_{10}(a_{ion}) \qquad (1)$$

Here, E is the potential measured from the sensor, E0 is the standard potential, R is the ideal gas constant, T is the temperature, F is Faraday's constant, z is the number of electrons transferred in reaction, and $a_{ion}$ is the ion activity. The ion activity is a function of the concentration of the ion in solution and the activity coefficient, which is 1 for sufficiently dilute solutions. Thus, a potentiometric sensor for a monovalent ion, such as nitrate, at room temperature is expected to exhibit a 59.1 mV change for every factor of ten change in concentration of the ion. For monovalent anions (z=−1), such as nitrate, this is a negative relationship where increasing concentration decreases potential.

FIG. 10 shows a photograph of the printed reference electrode 102 and ISE 104. Because the fabrication and operation of printed potentiometric sensors is simple, they could be widely distributed throughout a landscape to map the movement of nitrate through the watershed, inform efficient application of fertilizer, or alert residents to elevated nitrate levels in drinking water.

Figure 11:
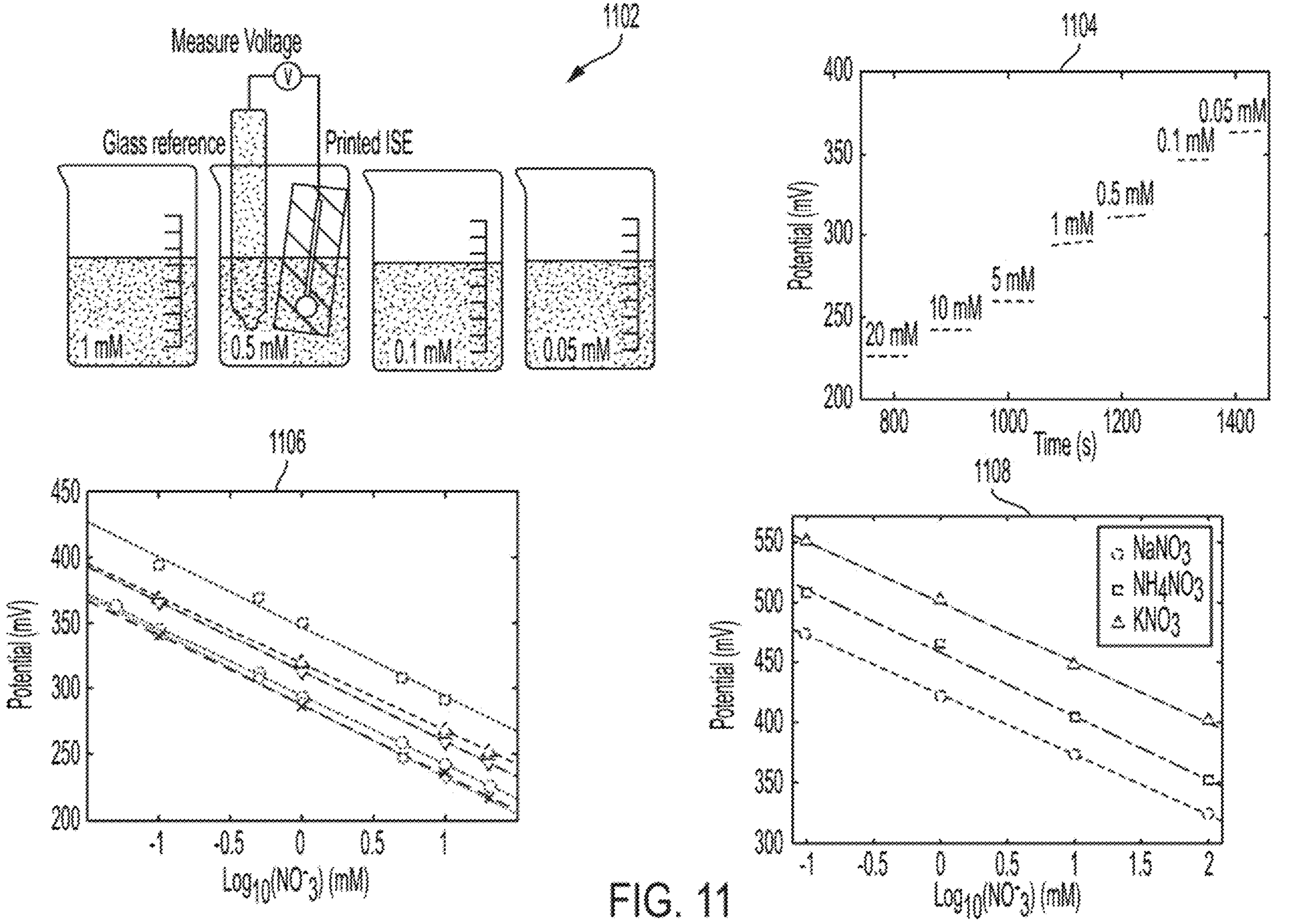
FIG. 11 illustrates example data collected from the printed potentiometric sensor of the present disclosure against commercial reference electrodes.

The sensitivity and selectivity of the ISE 104 alone was focused on by measuring the potential of the ISE 104 with respect to a commercial Ag/AgCl reference electrode 102, as shown in set up 1102 in FIG. 11. FIG. 11 also illustrates the potential of a nitrate sensor over time in decreasing concentrations of nitrate in graph 1104. This indicates that the sensors have a fast response time. Sensors showed no hysteresis. The range measured for the sensor is 0.05 mM nitrate to 20 mM nitrate, which corresponds to 3.2 to 1240 ppm.

The graph 1104 illustrates potential over time response of a printed nitrate sensor changing concentrations of nitrate. ISE is measured against a commercial Ag/AgCl reference electrode.

This response is repeatable from sensor to sensor, as shown by graph 1106 in FIG. 11 for six sensors. This shows close agreement from batch-to-batch.

These sensors have a near-Nernstian response of −53.3 mV/decade±1.1 mV/decade. These sensors maintain their sensitivity when lab-grade $NaNO_3$ is replaced with $KNO_3$ or $NH_4NO_3$ commercial fertilizers, as shown in graph 1108 in FIG. 11. For four sensors, the sensitivity in NH4NO3 was −51.2±4.0 mV/decade, and for $KNO_3$ sensitivity was −52.6±5.0 mV/decade.

A potentiometric chemical sensor should change potential only in the presence of the analyte of interest. To test selectivity of the printed nitrate sensor, the nitrate ISEs were measured against a commercial Ag/AgCl reference electrode in solutions of ions common to soils.

Screening experiments are an economical way to identify important factors in a system when a large number of potential variables may affect the response. The Definitive Screening Design is a three level experiment that can identify active factors using 2N+3 runs, where N is the number of factors being measured. The use of this design was demonstrated for selectivity testing of the printed ISE 104 against five ions common to soils.

Figure 12B:
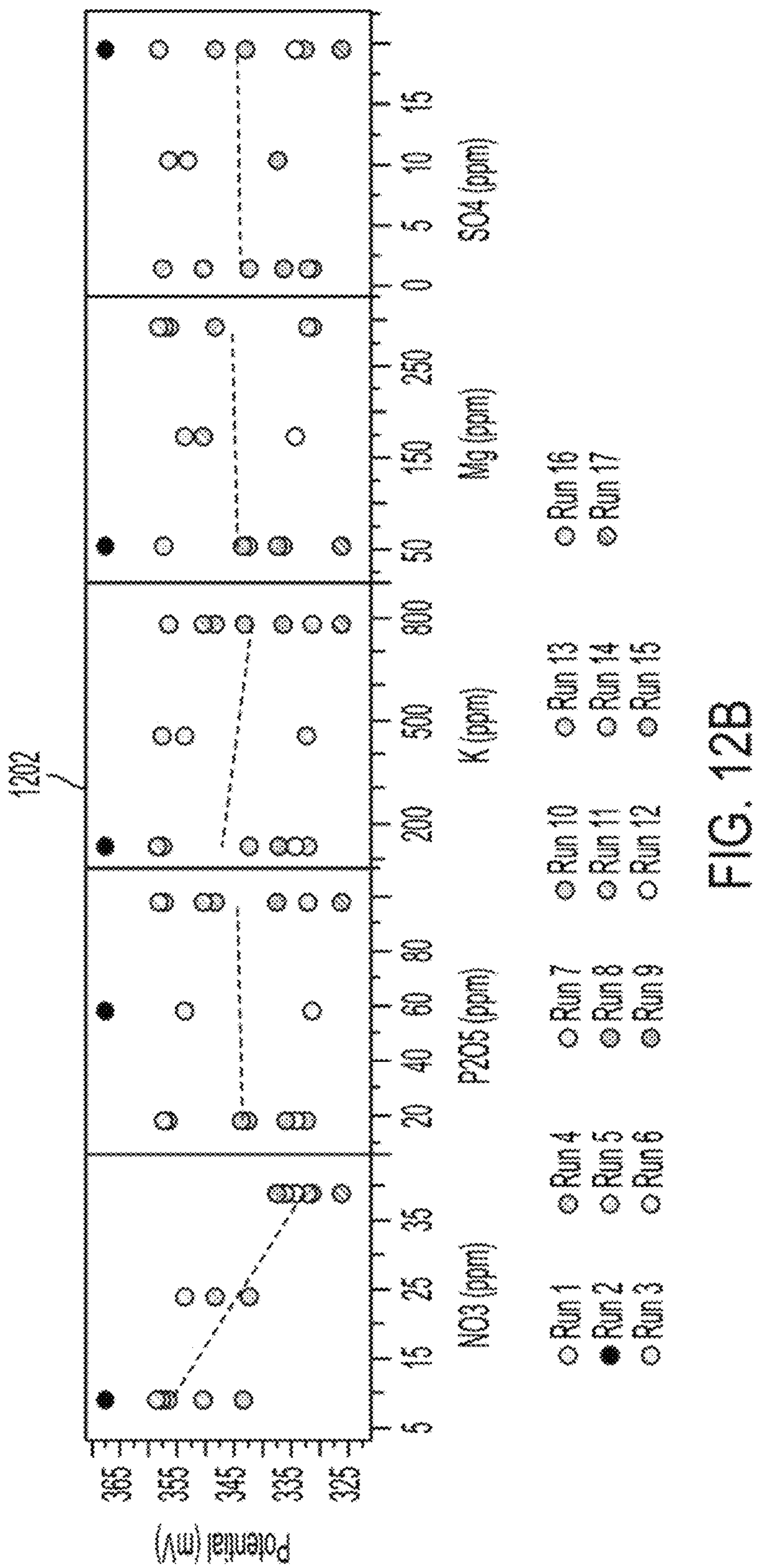

FIGS. 12A and 12B show the design structure of the experiment. Here, five factors (or ions) were used; namely $NO_3$, $P_2O_5$, $K^+$, $Mg^{2+}$ and $SO_4^{2-}$ as shown in table 1200. Four extra runs were added to increase the power of the experiment, resulting in 17 runs. Each run contains each of the five factors (ions) at either their low concentration, their high concentration, or at an intermediate concentration midway between the low and the high concentrations. For example, the factor $NO_{3\_}$ is run at 10 ppm (low concentration), 40 ppm (high concentration) and 25 ppm (intermediate concentration). The upper limits represent a maximum of what is considered barely excessive in soil in the western United States, while the lower limits are what is considered barely lacking. A single solution was made for each of the 17 runs outlined in table 1200. The potential of the ISE was measured against a commercial Ag/AgCl reference electrode in each solution to obtain the results in graphs 1202.

For these experiments, $NaNO_3$ was used as the source of $NO_3$ 192, commercially available water-soluble Monopotassium Phosphate Fertilizer (0-52-34) containing $P_2O_5$ and $K_2O$ was used as the source of P2O5, the same water-soluble fertilizer augmented with KCl was used as the source of K+, $MgCl_2$ was used as the source of $Mg^{2+}$, and $Na_2SO_4$ was used as the source of $SO_4^{2-}$.

Figure 13:
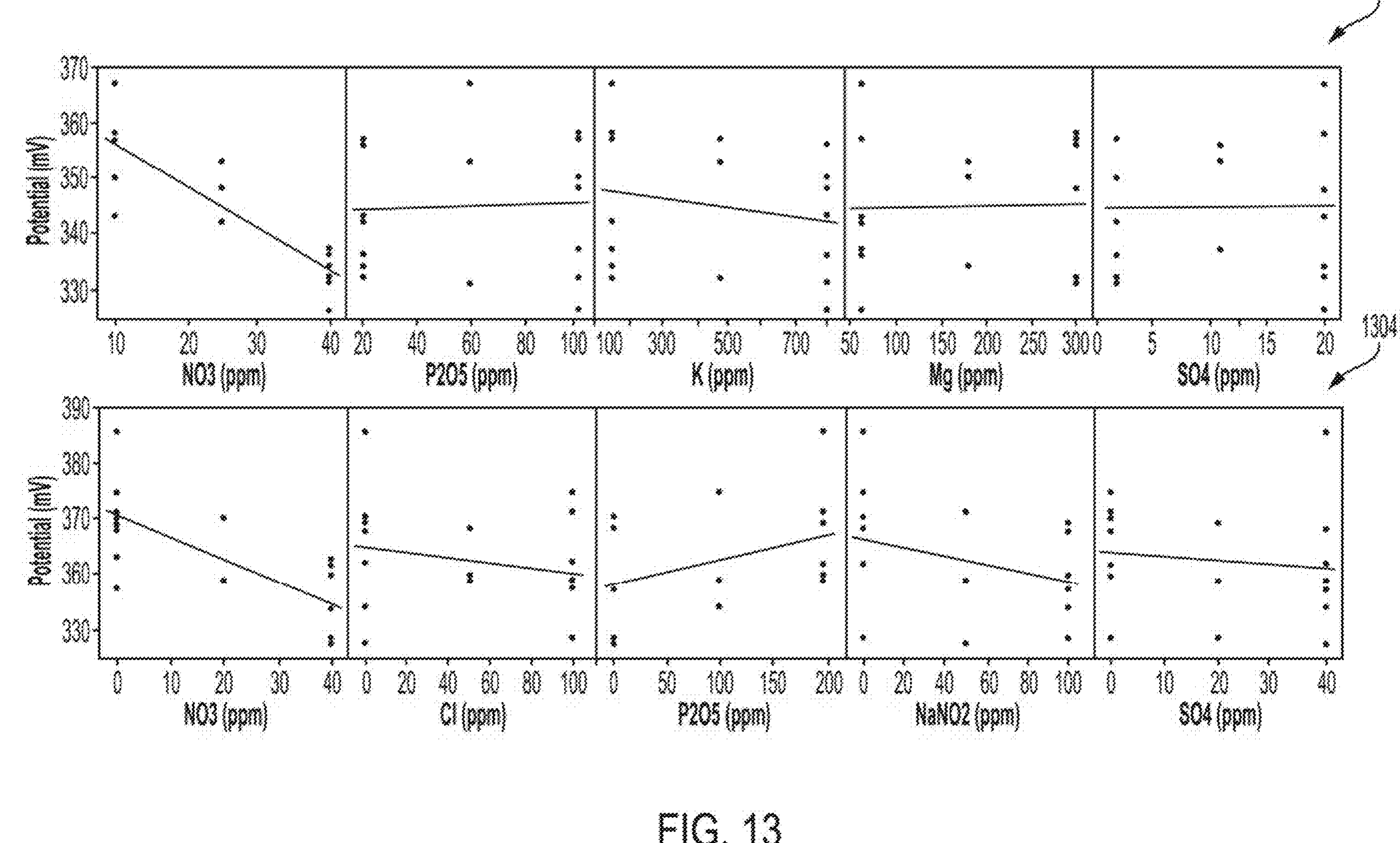
FIG. 13 illustrates example data from screening experiments.

In the graphs 1302 in FIG. 13, the experimental data is ordered by factor, and the slope of each line indicates the sensitivity of the ISE to the respective ion. Thus, a horizontal line suggests little interference. Statistical analysis showed only nitrate to have a significant effect on the nitrate sensor, which is visible in the nitrate graphs as a steeper best-fit line compared to those of the other ions.

A second definitive screening experiment was executed with the lower limits of each ion set to 0 ppm and upper limits set to twice what is considered excessive in soil in the western United States. The effects plot for the standard range of analyte concentrations is compared to the effects plot of the wide-range analyte concentrations in graphs 1304 of FIG. 13. The factor list has changed to eliminate co-dependence between factors, since the range of chemical concentrations was more than doubled. The experimental data showed $NO_3$, $P_2O_5$, and $NO_2$ to significantly affect sensor signal in the second experiment, though nitrate had the greatest effect.

Printed reference electrodes were also optimized. Because the reference electrode acts as electrochemical ground, it should not change potential in varying ionic environments. The precise composition of the printed reference electrode will impact E0 in the Nernst equation, but the absolute value of E0 matters less than the fact that it is constant with respect to nitrate concentration: A constant offset is easily accounted for in calibration while an unstable reference will impact the full sensor's sensitivity.

Figure 14A:
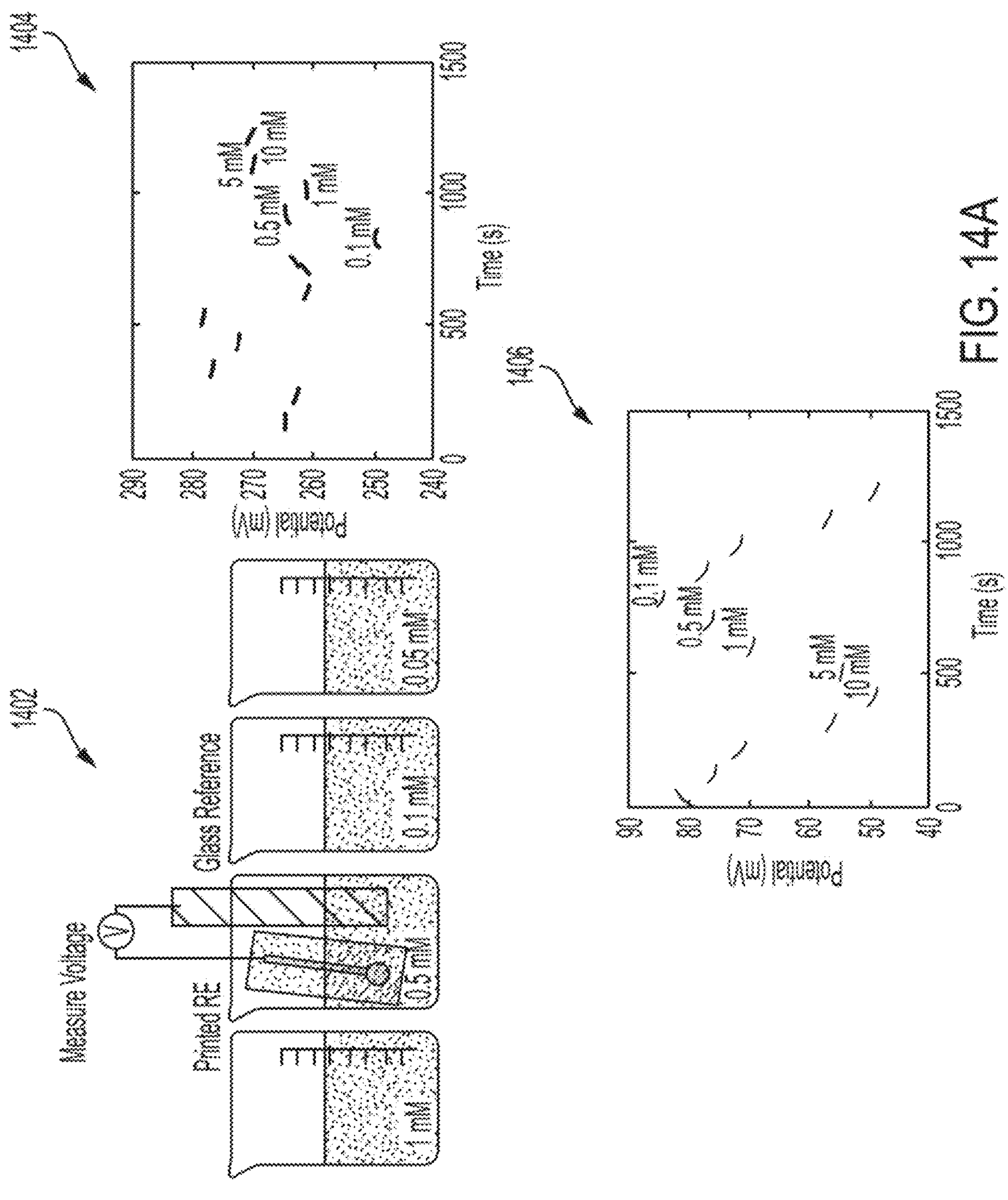
FIGS. 14A and 14B illustrate example data collected from a printed reference electrode of the present disclosure against commercial reference electrodes.

To optimize the printed references, they were measured against a commercial Ag/AgCl double junction reference, as shown in a setup 1402 illustrated in FIG. 14A. First, pristine printed Ag/AgCl electrodes were measured, and the resulting data is shown in graph 1404 in FIG. 14A. The output voltage is unstable because the printed reference lacks a source of chloride ions, which are needed for the reversible reaction AgCl+e−< >Ag+Cl−, which keeps the reference potential stable.

Next, printed references with a carbon nanotube layer to increase surface area and a PVB-NaCl membrane were tested in varying nitrate concentrations, with the results shown in graph 1406 in FIG. 14A. These electrodes used the formation developed for use in chloride-rich environments. They show a −18 mV/decade sensitivity to nitrate.

It has been shown in previous works that including the ion of interest in the membrane of a reference electrode reduces its sensitivity to that ion. To reduce sensitivity to nitrate, $NaNO_3$ was added to the PVB-NaCl membrane and sensitivity data for this electrode is shown in graph 1408 in FIG. 14B. This formulation has a sensitivity of −3 mV/decade, a marked improvement over the NaCl 235 membrane alone.

Figure 14B:
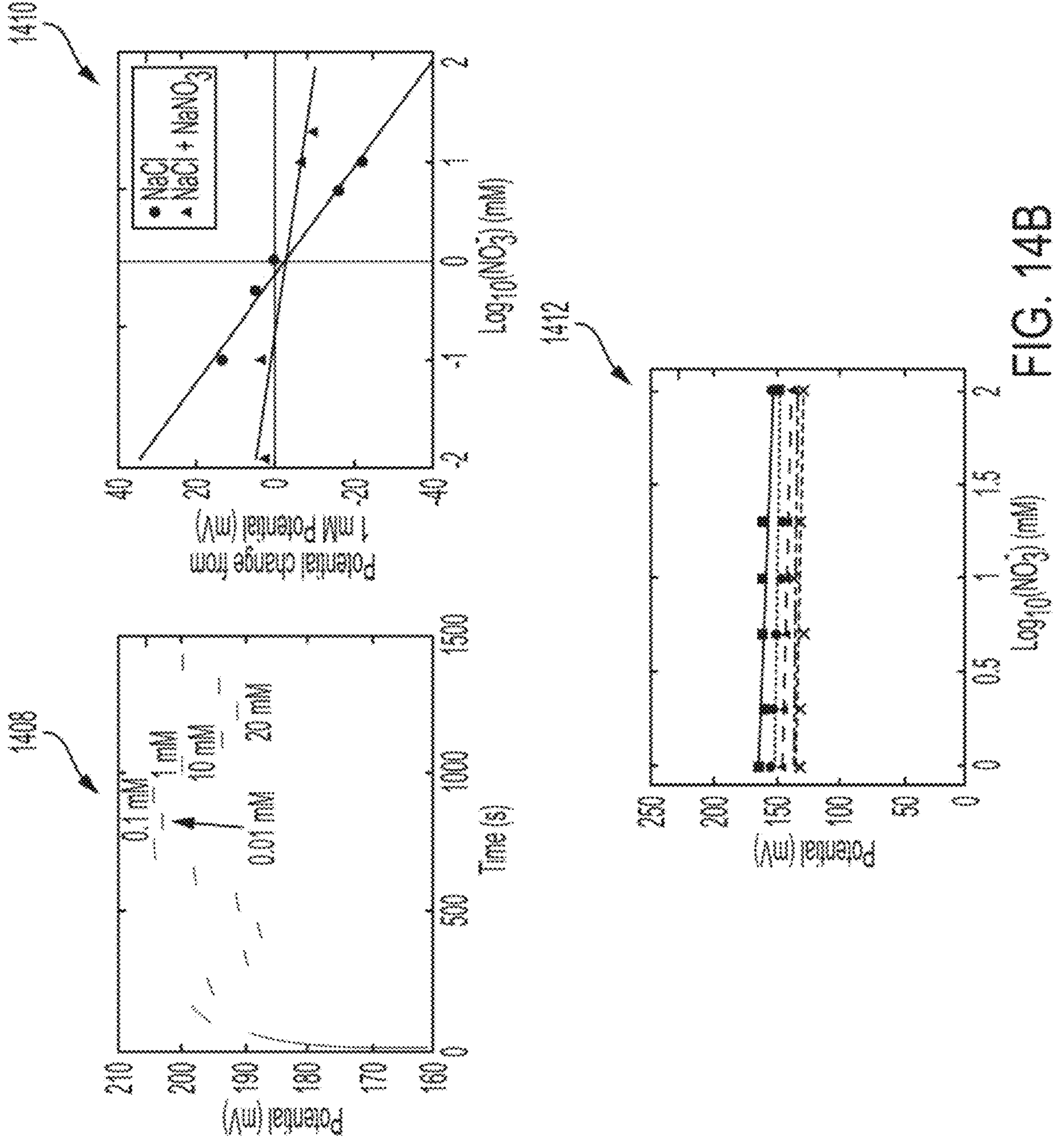

Graph 1410 in FIG. 14B shows sensitivity of the printed reference electrodes with NaCl in PVB membrane and $NaNO_3$ and NaCl in a PVB membrane.

Graph 1412 in FIG. 14B shows voltage vs concentration for five printed references with the NaCl+NaNO3+PVB membranes. All the printed references showed stable potential response despite over two orders of magnitude change in the nitrate concentration.

Once the printed ISE and the printed reference electrode had been optimized and characterized independently, they were paired to form a fully printed sensor. The sensitivity of the fully printed sensor was characterized in 0.01 mM to 100 mM NaNO3, and average sensitivity was found to be −50 mV/decade update this with more info after completing larger number of trials. This is comparable to the sensitivity of −53 mV/decade that was measured for the nitrate sensor with a printed ISE and commercial reference electrode.

Figure 15:
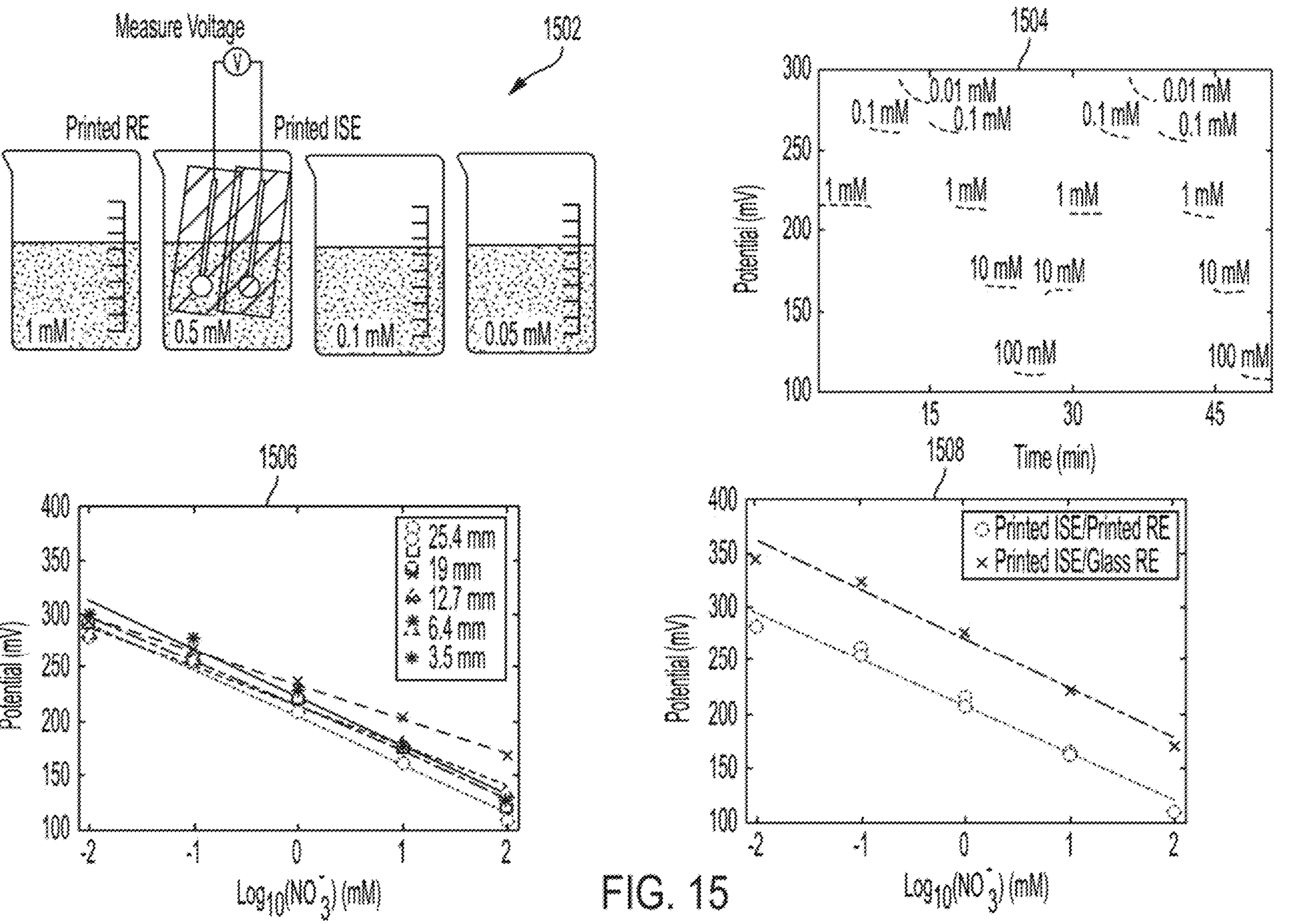
FIG. 15 illustrates data from a printed potentiometric sensor of the present disclosure.

Setup 1502 in FIG. 15 illustrates how fully printed sensor is measured. Graph 1504 illustrates the potential over time in changing concentrations of nitrate of a printed ISE versus a printed Ag/AgCl reference electrode. Graph 1506 shows the sensitivity of fully printed sensors in $NaNO_3$. Graph 1508 shows the sensitivity of the fully printed sensor is similar to that of a printed ISE paired with a glass reference. The fully printed sensor's potential is consistently 100 mV lower than that of the printed ISE/glass reference pair due to the reference potential offset of the printed reference.

In addition, printed potentiometric ammonium sensors were demonstrated. A reference electrode comprising of PVB and NaCl solution was drop-casted on the printed Ag/AgCl electrode with an intermediate CNT layer. The printed potentiometric ammonium also includes an ammonium ISM drop-casted onto the printed gold electrode. The constituents of the ISM are ammonium ionophore (nonactin), plasticizer (2-nitrophenyl octyl ether, o-NPOE), and polymer (PVC).

The printed ammonium sensors showed a near-Nernstian sensitivity of 57.4 mV/dec±4.7 mV/dec.

Although an example printing method is described above, other printing methods can be used to fabricate the printed potentiometric sensor 100 of the present disclosure. For example, other printing methods may include bar coating, blade coating, dip coating, drop casting, inkjet printing, screen printing, spin coating, and spray coating.

Figure 6:
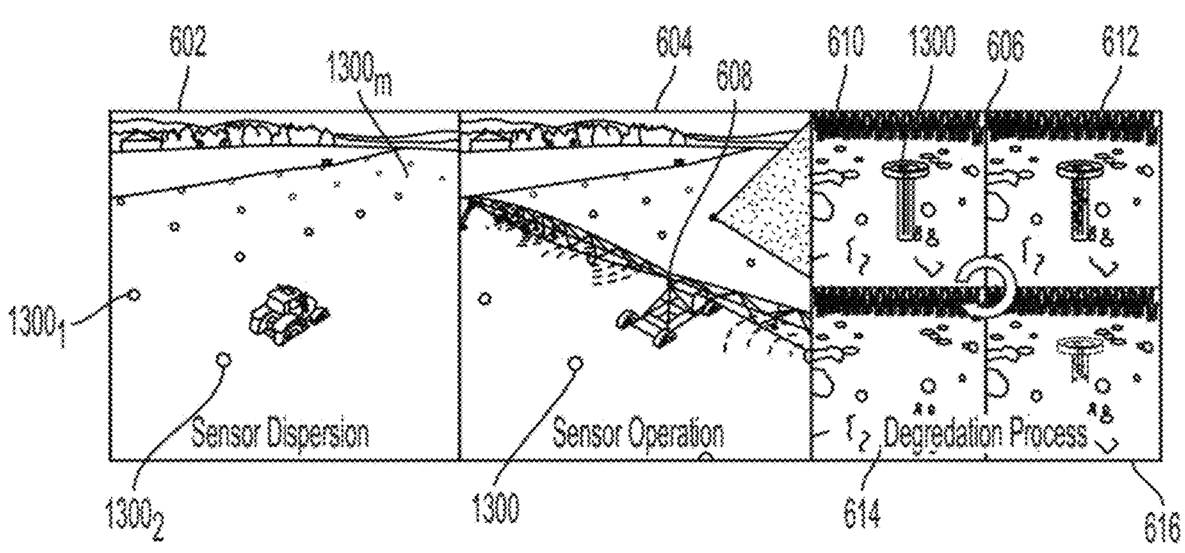
FIG. 6 illustrate an example of the sensors deployed in the soil and how the sensor can biodegrade in accordance with the present disclosure.

FIG. 6 illustrates an example of how the sensors 100 (e.g., via sensor assemblies 1300) can be dispersed in the soil over a wide area to measure and collect analyte data in image 602. For example, image 602 illustrates how a plurality of sensor assemblies $\mathbf{1300}_1$ to $\mathbf{1300}_m$ each having the sensors 100 can be dispersed in soil.

Depending on the analyte that is measured, the distance between sensors 100 may vary. For example, to provide an accurate measurement of phosphorous, the sensors 100 may be placed 30 meters apart. To provide an accurate measurement of nitrate, the sensors may be placed 85 meters apart. Once the sensors 100 are dispersed at the appropriate distances for the ions that are being measured, the sensors 100 of the present disclosure may provide a high-resolution data set that is accurate at a relatively low cost compared to other available methods such as satellite imaging or large singular analysis devices.

Image 604 of FIG. 6 illustrates how the sensors 100 may transmit data to a collection server 608. The collection server 608 may receive concentration data in the form of measured voltage from each sensor. The collection server 608 may then convert the measured voltage data into a concentration value for each particular ion that is being measured in the soil.

Image 606 also illustrates an example of how the sensor assembly 1300 may biodegrade over time in the soil. The image 606 includes different views of the sensor assembly 1300 at different points in time via images 610, 612, 614, and 616. As noted above, the printed potentiometric sensors may be printed with biodegradable materials. As a result, everything except the plastic polymer in the membrane layer of the electrodes 102 and 104 in the sensor 100 may be biodegradable. However, the membrane layer may account for less than 0.3% of the overall mass of the electrodes 102 and 104. Thus, a negligible amount of the electrodes 102 and 104 may remain even after the rest of the electrodes 102 and 104 have degraded over time.

In one embodiment, the substrate may be fabricated from thin-cut wood, biodegradable polymers, papers, or natural materials. Examples of thin-cut wood may include plywood, basswood, balsawood, pine, and the like. Examples of biodegradable polymers may include polylactic acid, polycaprolactone, polyhydroxybutyrate, poly(3-hydroxybutyrate-co-3-hydroxyvalerate), poly(glycolic acid), and the like. Examples of papers may include Bristol paper, copy paper, watercolor paper, filter paper, and the like. Examples of natural materials may include chitin, shellac, silk, and the like.

In one embodiment, the conductive particles in the membrane may include carbon allotropes or metals. Examples of the carbon allotropes may include carbon nanotubes, carbon black, graphite, graphene, and the like. Examples of the metals may include magnesium, manganese, tungsten, zinc, iron, and the like.

In one embodiment, the binder in the membrane may include polymers or waxes. Examples of the polymers may include carbomethyl cellulose, polycaprolactone, polylactic acid, polyvinyl propylene, phenol formaldehyde resin, and the like. Examples of the waxes may include beeswax, candelila wax, soy wax, coconut wax, myrtle wax, animal wax, and the like.

In one embodiment, the encapsulants may include polymers or waxes. Examples of the polymers may include polycaprolactone, polylactic acid, phenol formaldehyde resin, and the like. Examples of the waxes may include beeswax, candelila wax, soy wax, coconut wax, myrtle wax, animal wax, and the like. Thus, various combination of materials may be used for the various layers of the sensor 100 and/or the sensor assembly 1300 to allow the sensor 100 and/or the sensor assembly 1300 to be biodegradable.

Thus, the present disclosure provides potentiometric nitrate sensors comprising a printed reference and a printed ISE were designed and fabricated. A printed reference with relatively low sensitivity to nitrate was developed using a membrane composed of PVB with NaCl and $NaNO_3$. The printed nitrate sensors showed a near-Nernstian sensitivity of −53.3 mV/dec±1.1 mV/dec. These sensors were shown to be insensitive to common chemicals found in soil at average soil levels. However, these sensors experience interference at highly excessive concentrations of $P_2O_5$ and $NO_2$, which should be considered when applying these sensors in a region with high levels of these chemicals. Since these sensors are printed, the materials employed in this study can be substituted for degradable materials to realize a naturally degradable sensor.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. An apparatus, comprising:

a reference electrode, comprising:

a reference electrode substrate;

a reference electrode conductor formed via a printable composition on the reference electrode substrate;

a carbon nanotube layer formed on the reference electrode conductor; and a reference membrane formed on the carbon nanotube layer; and an ion selective electrode (ISE), comprising:

an ISE substrate;

an ISE conductor printed on the ISE substrate via a printable composition on the ISE substrate;

an ion-selective membrane printed on the ISE conductor via a printable membrane solution; and a solution ion-to-electron transduction layer formed on the ISE conductor between the ISE conductor and the ion-selective membrane.

2. The apparatus of claim 1, wherein the reference electrode substrate, the reference electrode conductor, the ISE substrate, the ISE conductor, and the ion-selective membrane comprise biodegradable materials.

3. The apparatus of claim 1, further comprising:

an encapsulant deposited over the reference electrode substrate and the reference electrode conductor.

4. The apparatus of claim 1, further comprising:

an encapsulant deposited over the ISE substrate and the ISE conductor.

5. The apparatus of claim 3, wherein the encapsulant comprises a biodegradable polymer or a wax.

6. The apparatus of claim 1, wherein the reference membrane comprises a structural polymer, a salt, and a chloride compound.

7. The apparatus of claim 6, wherein the ionophore is selected based on an ion that is to be detected by the ISE.

8. The apparatus of claim 1, wherein the ion-selective membrane comprises a structural polymer, a plasticizer, an ionophore, and a charge carrier.

9. The apparatus of claim 1, wherein the ISE conductor comprises the printable composition of a binder and conductive particles.

10. The apparatus of claim 9, wherein the binder comprises a wax.

11. The apparatus of claim 1, wherein the reference electrode substrate and the ISE substrate comprise at least one of: wood, a biodegradable polymer, or paper.

12. The apparatus of claim 1, wherein the reference electrode conductor and the ISE conductor comprise a carbon allotrope.

13. An apparatus, comprising:

a stake;

an antenna on the stake;

a reference electrode, comprising:

a reference electrode substrate;

a reference electrode conductor formed via a printable composition on the reference electrode substrate;

a carbon nanotube layer formed on the reference electrode conductor; and a reference membrane formed on the carbon nanotube layer;

at least one ion selective electrode (ISE), comprising:

an ISE substrate;

an ISE conductor formed on the ISE substrate formed via a printable composition on the ISE substrate, wherein the ISE conductor comprises the printable composition of a wax binder and conductive particles; and an ion-selective membrane formed on the ISE conductor; and a controller communicatively coupled to the antenna, the reference electrode, and the at least one ISE to determine an ion concentration based on measurements received from the at least one ISE and transmit the ion concentration to a server via the antenna.

14. The apparatus of claim 13, wherein the stake, the reference electrode substrate, the reference electrode conductor, the ISE substrate, the ISE conductor, and the ion-selective membrane comprise biodegradable materials.

15. The apparatus of claim 13, wherein the at least one ISE comprises an array of ISEs to measure different ions.

16. The apparatus of claim 13, further comprising:

an encapsulant deposited over the reference electrode substrate and the reference electrode conductor in the reference electrode and over the ISE substrate and the ISE conductor in the at least one ISE.

17. The apparatus of claim 13, wherein the at least one ISE further comprises:

a solution ion-to electron transduction layer formed on the ISE conductor between the ISE conductor and the ion-selective membrane.

18. A method of fabricating a sensor, comprising:

providing an ion selective electrode (ISE) substrate;

printing a conductive trace on the ISE substrate;

applying an encapsulant with an opening over the conductive trace and the ISE substrate, wherein the opening exposes a portion of the conductive trace;

depositing an ISE membrane via a drop cast process onto the portion of the conductive trace exposed through the opening of the encapsulant to form an ISE; and providing a solution ion-to-electron transduction layer trace between the conductive trace and the ISE membrane.

19. The method of claim 18, further comprising:

printing a reference electrode; and assembling the reference electrode, the ISE, a controller, and an antenna on a stake, wherein the controller is communicatively coupled to the antenna and the conductive trace of the ISE and a conductive layer of the reference electrode.

20. The method of claim 18, wherein the conductive trace comprises a printable composition of a wax binder and conductive particles.

* * * * *